United States Patent [19]

Åkerlöf et al.

[11] Patent Number: 5,304,464
[45] Date of Patent: Apr. 19, 1994

[54] PROTEIN COMPLEX ENHANCING SPERM MOTILITY

[75] Inventors: Eva Åkerlöf, Midgardsvägen 13, S-141 39 Huddinge; Åke Pousette, Mickelsbergsvägen 113, S-125 32 Älvsjö, both of Sweden

[73] Assignees: Eva Åkerlöf, Huddinge; Åke Pousette, Älvsjö, both of Sweden; Applied Research Systems ARS Holding N.V., Curacao, Netherlands

[21] Appl. No.: 777,277
[22] PCT Filed: Apr. 2, 1990
[86] PCT No.: PCT/SE90/00213
 § 371 Date: Nov. 27, 1991
 § 102(e) Date: Nov. 27, 1991
[87] PCT Pub. No.: WO90/12032
 PCT Pub. Date: Oct. 18, 1990

[30] Foreign Application Priority Data

Mar. 31, 1989 [SE] Sweden ............................ 8901127

[51] Int. Cl.⁵ .................. A01N 1/02; A61K 37/10
[52] U.S. Cl. ........................ 435/2; 524/520; 524/531; 514/8; 514/21
[58] Field of Search ............... 424/520, 531; 514/8, 514/21; 435/2, 4

[56] References Cited

U.S. PATENT DOCUMENTS 4,511,558  4/1985  Shur .................................... 514/8
4,804,537  2/1989  Bergman ........................... 424/105

OTHER PUBLICATIONS

Scopes Robert R, Protein Purification, Springer-Verlag N.Y. 1982 pp. 101–105, 111–113.
Chemical Abstracts, vol. 111, No. 7, Aug. 1989, (Columbus, Ohio, US), Eva Aakerloef et al.: "Serum factors stimulate the motility of human spermatozoa", see p. 497, abstract 54821x, & Int. J. Androl. 1989, 12 (2), 124–130.

Primary Examiner—Michael G. Wityshyn
Assistant Examiner—Ralph Gitomer
Attorney, Agent, or Firm—Browdy and Neimark

[57] ABSTRACT

The present invention relates to a macromolecule of proteinaceous nature which activates sperm motility, a process for the preparation thereof by purification of the macromolecule from extracellular fluids, pharmaceutical preparations containing the macromolecule and antibodies directed against determinants specific to the macromolecule and the use thereof as a method to assay the potential fertility of sperm.

5 Claims, 5 Drawing Sheets

FIG. 1A
ION-EXCHANGE CHROMATOGRAPHY

FIG. 4B

PROTEIN COMPLEX ENHANCING SPERM MOTILITY

FIELD OF INVENTION

The present invention relates to a macromolecule of proteinaceous nature which activates sperm motility, a process for the preparation thereof by purification of the macromolecule from extracellular fluids, pharmaceutical preparations comprising the macromolecule and antibodies directed against determinants specific to said macromolecule.

BACKGROUND ART

It is previously known that only spermatozoa with a good ability to move and with a relatively straightlined progressive motility have the possibility to achieve fertilization and that only the spermatozoa with the best morphology enter the cervical mucus (Fredricsson B. and Björk G. (1977): Morphology of postcoital spermatozoa in the cervical secretion and its clinical significance. Fertil. Steril. 28:841–845). It is also previously known that serum support sperm motility /Austin R. (1985) "Sperm maturation in the male and female genital tracts." In: Biology of Fertiliztion, vol. 2 (eds C Metz and A Monroy) pp. 121–147, Academic Press, New York/ and is therefore used in connection with sperm separation for fertilization in vitro.

However, there are problems inherent in the use of a fluid comprising thousands of components and a specific active component would give a safer and more predictible effect than such a fluid. An active factor would also give the effect without dangerous concomittant actions e.g. immunologic factors or infectious diseases.

DISCLOSURE OF INVENTION

During work with fertilization, in vitro standardized model systems were developed for e.g. sperm motility test, to obtain more homogeneous populations of motile and viable spermatozoa and to analyze the adenosinetriphosphate (ATP) content of sperm and its specific progressive motility (SPM): Åkerlöf E., Fredricsson B., Gustafson O., Lundin A., Lunell N-O., Nylund L., Rosenborg L. and Pousette Å (1987) Int. J. Androl. 10, 663–669 and Pousette Å., Åkerlöf E., Lundin A., Rosenborg L. and Fredricsson B. (1986) Int. J. Androl. 9, 331–340.

Said standardized model systems became the tools for the further investigation of serum to find the factor or factors giving the motility activity to the sperm necessary for the fertilization to take place. Through an extensive research work the present inventors have now found that sperm motility is activated by a macromolecule having a molecular weight of about 200,000 Daltons.

Said macromolecule is of proteinaceous nature, essentially pure and activates sperm motility. The molecular weight of said protein is according to a preferred embodiment of the invention about 180,000 Daltons.

A further preferred embodiment of the invention discloses a proteinaceous macromolecule having an isoelectric point of about 5.1 and comprising albumin. The molecular weight of said macromolecule is preferably about 250,000 Daltons.

The macromolecule according to the invention is substantially homogeneous and obtainable from extracellular fluids, particularly from serum of animals or human beings.

The proteinaceous macromolecule is purified from extracellular fluids from animals or human beings, preferably from serum and according to a preferred embodiment from serum of human beings.

According to a further preferred embodiment a proteinaceous macromolecule having an isoelectric point of about 5.1 and comprising apolipoprotein Al, immunoglobulin and albumin is purified through a three step process comprising Ion-exchange Chromatography, Chromatofocusing and Fast Protein Liquid Chromatography (FPLC a system from Pharmacia LKB Biotechnology).

According to another preferred embodiment a proteinaceous macromolecule having a molecular weight of about 180,000 Daltons and comprising apolipoprotein Al and immunoglobulin is prepared by a four step purification process comprising Ion-exchange Chromatography, Chromatofocusing, Fast Protein Liquid Chromatography and Affinity Chromatography.

According to a yet further preferred embodiment the sperm motility activity is checked after every single purification step.

The invention is also relating to pharmaceutical preparations comprising a macromolecule of proteinaceous nature which is essentially pure, has a molecular weight of about 200,000 Daltons and activates sperm motility together with any suitable excipient.

Examples of suitable excipients are culture media or other salt solutions.

The pharmaceutical preparations are prepared according to methods known per se. The pharmaceutical preparations according to the invention are used in the treatment of infertility, preferably in-vitro.

The invention further comprises a method to determine the potential fertility of sperm by treating a sample with a macromolecule according to the invention and compare its motility against a known standard.

The invention also comprises antibodies directed against determinants specific to the macromolecule according to the invention, preferably polyclonal antibodies obtainable by immunizing according to methods known per se. Said antibodies are used as a tool in the process and can further be used as a means for the preventing of fertilization by inhibiting the sperm motility activating properties.

The SPAP was purified from serum obtained from male blood donors and incubated at 56° C. for 30 minutes before storage at −20° C. until use.

According to one embodiment of the invention the purification process was performed in three steps and revealed a macromolecule comprising apolipoprotein Al, Ig and albumin in about equimolar amounts and having a molecular weight of about 200.000 Daltons or more precisely about 250,000 Daltons, and an isoelectric point of about 5.1.

Said steps were:

1. Ion-exchange chromatography on DEAE-Sepharose ® (ion exchange material from Pharmacia Fine Chemicals) and elution with a linear NaCl gradient, 0–0.25 mol/l.
2. Chromatofocusing on PBE TM 94 (Polybuffer exchanger for chromatofocusing from Pharmacia Fine Chemicals) with histidine-HCl as the starting buffer. The pH interval was 6.0–4.0.
3. Fast Protein Liquid Chromatography (FPLC ®, Pharmacia) on two Superose ® (Prepacked column with Superose for FPLC; Superose is a cross-linked, agarose-based medium for gel filtration) 12 HR 10/30 columns (serially) with molecular weight separation. According to a yet preferred embodiment of the invention by addition of a fourth step such as Affinity chromatography on Blue Sepharose ® (A freeze dried powder from Pharmacia, Sweden) a SPAP comprising apolipoprotein Al and immunoglobulin with a molecular weight of about 180,000 Daltons is obtained.

To follow the occurence of the sperm motility activity in serum fraction after every single purification step the preparations were submitted to a specific progressive motility (SPM) test and sodium dodecyl sulphate (SDS) polyacrylamide gel electrophoresis. For the preparation of a macromolecule comprising apolipoprotein Al and Ig a four-step protocol, including Ion-exchange (DEAE-Sepharose ®) Chromatography, Chromatofocusing, exclusion FPLC ® (elution corresponding to a molecular weight of about 250 kD) and Blue Sepharose ® Chromatography (no binding but elimination of albumin) was used. The pure protein, at a concentration of 20–70 nmol/l, activated the motility to the same extent as serum.

SDS polyacrylamide gel electrophoresis under non-reducing conditions showed one band corresponding to a molecular weight of about 180 kD. In the presence of mercaptoethanol the fraction after Blue-Sepharose gave two bands corresponding to 50 kD and about 25 kD. Without the Blue Sepharose ® step the non-reduced complex eluted as a larger component and after reduction SDS polyacrylamide gel electrophoresis then revealed an additional band at about 67 kD, suggesting that the molecule is then in complex with albumin, the latter being removed by the Blue Sepharose ® step. Amino acid sequence analysis of the Blue Sepharose ® eluate, identified three protein chains—those of apolipoprotein Al and immunoglobulin heavy and light chains—suggesting that the preparation was an apolipoprotein Al-immunoglobulin complex. Antiserum, raised in a rabbit, inhibited sperm motility, when added directly to spermatozoa. Pretreatment of human serum with rabbit antiserum, significantly reduced its ability to activate sperm motility. The sperm activating capacity of the protein complex was destroyed by heating at 100° C. for 5 minutes, suggesting that the activity was dependent on intact protein conformations. Albumin, apolipoprotein Al and immunoglobulins by themselves had only minor effects on sperm motility. It appears likely that an apolipoprotein Al-immunoglobulin complex, mediates activation of sperm motility.

In this context the following abbreviations are used:

| | |
|---|---|
| ApoAl | Apolipoprotein Al |
| ATP | Adenosine triphosphate |
| D | Dalton |
| FPLC ® | Fast Protein Liquid Chromatography |
| HEPES | N-2-Hydroxyethylpiperazine-N'-2-ethanesulphonic acid |
| Ig | Immunoglobin |
| IVF | In Vitro Fertilization |
| MW | Molecular Weight |
| SDS | Sodium Dodecyl Sulphate |
| SPAP | Sperm Activating Protein |
| SPM | Specific Progressive Motility |
| v/v | volume/volume |

BRIEF DESCRIPTION OF THE DRAWINGS

FIG. 1-A illustrates Ion-exchange (DEAE-Sepharose ®) Chromatography. Serum was applied to a DEAE-Sepharose ® column and eluted with a linear gradient 0–0.25M NaCl. Fractions were collected and the A 280 monitored. Aliquots of all fractions were assayed for SPM. The sperm activating capacity was eluted at about 0.2M NaCl.

FIG. 1-B illustrates Chromatofocusing on PBE TM 94. After dialysis against the starting buffer the pooled fractions were added to the PBE TM 94 chromatofocusing column and Polybuffer ® 74, (Polybuffer exchanger for chromatofocusing from Pharmacia Fine Chemicals) pH 4.0 was applied. Fractions were collected and monitored for pH and SPM. The sperm activating capacity was eluted at pH 5.1.

FIG. 1-C illustrates FPLC ®. The pooled fractions were dialysed, lyophilized (dissolved in water) and fractionated on two Superose ® 12 HR 10/30 columns (serially). The columns were calibrated using ready made standards (Pharmacia Fine Chemicals, Uppsala, Sweden). A part from every fraction was tested for SPM. The sperm activating capacity was eluted corresponding to a molecular weight of about 250 kD.

Lane 1: Phosphorylase b (94,000), Albumin (67,000), Ovalbumin (43,000), Carbonic Anhydrase (30,000), Trypsin Inhibitor (20,100) and Lactalbumin (14.400)

Lane 2: FPLC ® eluate with protein fraction (in the presence of 2-mercaptoethanol)

Lane 3: Thyroglobulin (330,000), Ferritin (220,000), Albumin (67,000), Catalase (60,000), Lactate Dehydrogenase (36,000) and Ferritin (18,500)

Lane 4: FPLC ® eluate with protein fraction in the absence of 2-mercaptoethanol. SDS polyacrylamide gel electrophoresis under non-reducing conditions showed one band corresponding to a molecular weight of about 180 kD. In the presence of mercaptoethanol this fraction gave two bands corresponding to 50 kD (later identified as immunoglobulin heavy chain) and about 25 kD (later identified as apolipoprotein Al and immunoglobulin light chain). Without the Blue Sepharose ® step the non-reduced complex eluted as a larger component and after reduction, SDS polyacrylamide gel electrophoresis revealed an additional band at about 67 kD, suggesting that the molecule is then in complex with albumin, the latter being removed by the Blue Sepharose ® step.

Lane 1: As lane 1 FIG. 2

Lane 2: Normal serum

Lane 3: Blue Sepharose ® eluate with protein fraction

Lane 4: As lane 3 FIG. 2

Lane 5: FPLC ® eluate with albumin fraction

Lane 6: FPLC ® eluate with protein fraction.

FIGS. 4A–4B illustrate the effect of the purified SPAP on SPM (FIG. 4A) and ATP content (FIG. 4B). Sperm were separated using the Percoll ® (Colloidal silica coated with polyvinylpyrrolidone, a medium for density gradient centrifugation of cells) technique and transferred to Buffer B. Purified SPAP was added in increasing concentrations to aliquotes of the sperm solution and spermatozoa were assayed for motility, 2.5 and 5 hours later and for ATP content 2 and 3 hours after addition of SPAP.

BEST MODE FOR CARRYING OUT THE INVENTION

The model for sperm motility test is explained in the following.

SEMEN SAMPLES

Ejaculates and blood sera were collected from six donors and were analyzed within 2 hours. /Fredricsson B. (1979) Andrologi 11, 57–61/. Separation of motile spermatozoa was achieved by self migration using a swim-up technique or a Percoll® gradient technique followed by translocation of spermatozoa to a defined culture medium. /Åkerlöf E., Fredricsson B., Gustafson O., Lundin A., Lunell N-O., Nylund L., Rosenborg L., and Pousette Å (1987) Int. J. Androl. 10, 663–669/.

For the swim-up preparation, 0.3 ml semen was covered with 1 ml tissue culture medium, RPMI-1640 (Flow) supplemented with 13% (v/v) male human serum, 24 mM HEPES (Sigma, USA), 50 IU/ml Penicillin and 50 µg/ml Streptomycin (GIBCO, Scotland) (Buffer B). After incubation at 37° C. for 45 minutes, the uppermost 0.5 ml containing motile sperm was harvested. For the Percoll® gradient technique, 1 ml of the ejaculate was layered gently on top of a Percoll® gradient. After 3 hours at 37° C. (without centrifugation) the upper part was sucked off and discarded, and the lower 3 ml were suspended. /Pousette Å., Åkerlöf E., Lundin A., Rosenborg L. and Fredricsson B. (1968) Int. J. Androl. 9, 331–340.

The fractions from 5–10 tubes (separated by swim-up or Percoll®) were pooled and added to a pump-filter system /Åkerlöf E., Fredricsson B., Gustafson O., Lundin A., Lunell N-O., Nylund L., Rosenborg L., and Pousette Å. (1987) Int. J. Androl. 10, 663–669/, in order to translocate motile spermatozoa to Buffer A (Buffer B without serum).

After dilution to about 3 million spermatozoa/ml, aliquots of 0.5 ml were transferred and 0.1 ml portions of Buffer A (control), serum (control), different additions or eluates from the purification steps were added. During establishment of the protocol for purification of the protein complex, progressive motility was assayed at different time intervals. For routine preparations, motility was measured 4–6 hours after addition of the test solutions, as the unspecific effect of albumin is minimized at this time.

ADDITIVES

Serum (used as control in sperm motility test as an additive in Buffer B), was incubated at 56° C. for 30 minutes and stored at −20° C. until use. Normal rabbit sera, rabbit anti-protein complex serum as well as immunoprecipitated sera were added directly or in different combinations to the sperm motility test.

Purified human apolipoprotein Al (A-9284 Sigma, Mo., USA) was dissolved in Buffer A to 1.7 g/l and added to the sperm motility test, giving final concentrations of 0.04–0.3 g/l in the test tubes. Gammonativ® (a pharmaceutical preparation containing human immunoglobulin and albumin, from Kabi, Stockholm, Sweden) was submitted to Blue Sepharose® chromatography to remove the albumin. The immunoglobulin was freeze-dried, dissolved in water and added to the sperm motility test.

MOTILITY

Progressive motility was analysed as described. /Pousette Å., Åkerlöf E., Rosenborg L. and Fredricsson B. (1986) Int. J. Androl. 9, 1–13/. The number of spermatozoa passing a specific line of known length in a Bürker chamber per unit of time was counted. Knowing the concentration, results have been expressed as passages per minute per million spermatozoa/ml. This value is termed the specific progressive motility (SPM). Sperm motility was assyed using aliquots from every fraction eluted. The motility was usually assayed 4–6 hours after addition of spermatozoa to avoid the initial increase in sperm motility that can be observed after addition of e.g. albumin.

ATP content was analysed in the "standardized model system" described in Pousette Å., Åkerlöf E., Lundin A., Rosenborg L., and Fredricsson B. (1986) Int. J. androl. 9, 331–340 and specific ATP defined as content of ATP (expressed in moles) per spermatozoon.

For the purification of SPAP sera from male blood donors were incubated at 56° C. for 30 minutes before storage at −20° C. until used for purifications. Fractions were dialysed and/or lyophilized before assayed for sperm activating capacity in the "standardized model system".

Ion-exchange Chromatography, Serum (100) was fractionated on a 100 ml DEAE-Sepharose® column (Pharmacia Fine Chemicals, Uppsala, Sweden) equilibrated in 0.01M phosphate buffer, pH 7.4. The serum was diluted two-fold with 0.01M phosphate buffer, pH 7.4, and added to the column. After washing, a linear gradient of 2×300 ml 0–0.25M NaCl in 0.01M phosphate buffer, pH 7.4, was applied. Fractions (about 5 ml) were collected and the absorbancy at 280 nm was monitored. Aliquots of all fractions were then dialysed against 0.125M phosphate buffer, pH 7.4, and assayed for ability to stimulate SPM. Fractions able to promote sperm motility were pooled. Usually about 10 fractions (50 ml) recovered at about 0.2M NaCl in the gradient were used for further purification.

CHROMATOFOCUSING ON PBE TM 94.

The pooled fractions were lyophilized, dissolved in 5 ml water, dialysed against the starting buffer (0,025M histidine-HCl, pH 6.0) and added to a 37 ml PBE TM 94 chromatofocusing column. After washing, Polybuffer®74, pH 4.0, was applied and fractions were monitored for pH and sperm activating capacity. Samples (1 ml of each fraction) were dialysed against 0.01M phosphate buffer, lyophilized and dissolved in 250 µl 0.125M phosphate buffer, pH 7.4, before added to the test for sperm motility. Fractions showing sperm activating capacity were pooled. Usually about 3 fractions (15 ml), eluted at about pH 5.1, were obtained.

FAST PROTEIN LIQUID CHROMATOGRAPHY® (FPLC)®

The fractions pooled were dialysed against 0.001M phosphate buffer, pH 7.4, and lyophilized, dissolved in 200 µl distilled water (Millipore®) and fractionated on two Superose® 12 HR 10/30 columns (serially) equilibrated in 0.125M phosphate buffer, pH 7.4. Calibrations were performed using ready made standards (Pharmacia Fine Chemicals, Uppsala, Sweden). A part (10 µl) from every fraction (600 µl) was tested for sperm activating capacity. Usually the activity was found in two fractions (1.2 ml) corresponding to a molecular weight of about 250 kD.

BLUE SEPHAROSE ® CHROMATOGRAPHY

The pooled fractions after FPLC ® were added to a Blue Sepharose ® column (10×20 mm) equilibrated in 0.125M phosphate buffer, pH 7.4. The sperm activating capacity did not stick to the gel and was recovered in the fractions corresponding to the void volume and the wash with 0.125M phosphate buffer, pH 7.4 (total: 30 ml). This material was lyophilized and dissolved in 1.0 ml water; ten µl was routinely used for the sperm motility test.

Analytical disc electrophoresis in the presence of sodium dodecyl sulphate (SDS) (NaDodSO$_4$), in the presence of (reducing) and in absence of 2-mercaptoethanol was performed using the GE 2/4 Vertical System (Pharmacia, Sweden) with ready made Gel Casette Kits (80×80 mm) in addition to standard for calibration (Pharmacia Fine Chemicals, Uppsala, Sweden). Proteins were visualised using Coomassie Blue. Samples for amino acid sequence analysis were degraded in an Applied Biosystems 470 A gas phase sequencer equipped with an on-line phenylthiohydantoin analyser 120 (Applied Biosystems Inc., Forster City, Calif.).

Quantitation of total protein was performed with the BIO-RAD protein assay a method for quantitation of total protein from (BIO-RAD Laboratories, München, GFR) using bovine serum albumin as standards. Apolipoprotein Al was analyzed with nephelometry using reagents from Behringwerke (Marburg, GFR).

Immunization and Immunoprecipitation were performed on two 1-year-old male New Zealand White rabbits as described/Vaitukaitis I. Robbins J B, Nieschlag E and Ross G T. (1971), J. Clin. Endocrinol. Metab. 33, 988–991/with the purified protein complex. The protein, 20 µg for one animal and 80 µg for the other, in 1 ml water was mixed with 1 ml Freund's complete adjuvant and the mixture was injected subcutaneously on the back of the animals. After 10 weeks, antiserum was detected in the rabbit given 20 µg SPAP.

Normal inactivated male serum and rabbit anti-SPAP serum were mixed in proportions ranging between 1:19 to 19:1 (v/v). The mixture was incubated at 25° C. for 20 hours before the tubes were centrifuged at 1400×g for 25 minutes. The supernatants removed by sucktion and the pellets formed were stored at −20° C. until used. The supernatants were tested for sperm motility and analyzed for apolipoprotein Al.

Amino acid sequence analysis were performed with two different pools each of three preparations of SPAP from the Blue Sepharose ® step were analyzed by amino acid sequence degradation. Results obtained were highly similar, establishing reproducibility of preparations, and revealed the presence of three major N-terminal sequences, which were followed for about 25 cycles before all were difficult to trace against a fairly high background (cf. Table I).

TABLE I

Amino acid sequence analysis of SPAP. Degradation of two preparations revealed three major N-terminal sequences in average ratios of about 1.4:1.1:1.0 that could be interpreted for 26, 20 and 15 cycles, respectively, before high background, carry-over and residue coincidences in the different structure prevented safe assignments. For the triplets identified at each cycle, the assignment as to sequence I, II and III respectively, was frequently ambiguous from recoveries only, but listing as belonging to I, II, III was easily assigned once the various combinations were found to fit into three known structures. I corresponds to apolipoprotein Al, II to immunoglobulin light chains (k), and III to immunoglobulin heavy chains (g, m and a). Residues identified at each cycle are listed in that order. At a few positions (1, 7, 11) only two major residues were identified (one in higher yield), reflecting positions where two of the structures appeared to have identical residues. Recoveries are split accordingly in their listing. Assignments considered tentative, mainly because of considerable gackground, are given within parenthesis. Two preparations gave almost identical results, except for slight variation in yields of individual residues, tentative assignments, and lengths of safe sequence tracings.

| Cycle | I | II | III |
|---|---|---|---|
| 1 | Asp 250 | (Asp 200) | Glu 200 |
| 2 | Glu 240 | Ile 190 | Val 180 |
| 3 | Pro 200 | Val 170 | Gln 200 |
| 4 | Pro 210 | Met 170 | Leu 200 |
| 5 | Gln 190 | Thr 150 | Val 140 |
| 6 | Ser 150 | Gln 130 | Glu 130 |
| 7 | Pro 160 | Ser 110 | Ser 110 |
| 8 | Trp 50 | Pro 140 | Gly 130 |
| 9 | Asp 150 | Val 140 | Gly 120 |
| 10 | Arg 100 | Thr 110 | (Glu 100) |
| 11 | Val 210 | Leu 90 | Leu 90 |
| 12 | Lys 170 | Ser 100 | Val 110 |
| 13 | Asp 140 | (Val 100) | Gln 80 |
| 14 | Leu 170 | Ser 80 | Pro 100 |
| 15 | Ala 150 | (Pro 90 | Gly 90 |
| 16 | Thr 100 | (Gly 80) | |
| 17 | Val 140 | Glu 60 | |
| 18 | Tyr 130 | Arg 50 | |
| 19 | Val 130 | Ala 70 | |
| 20 | Asp 100 | Thr 60 | |
| 21 | Val 130 | | |
| 22 | Leu 110 | | |
| 23 | Lys 80 | | |
| 24 | Asp 90 | | |
| 25 | Ser 70 | | |
| 26 | Gly 80 | | |

The triplets for each position were screened against known structures, revealing that the three protein structures were known before. Thus one, corresponded exactly to human apolipoprotein Al/Baker H. N., Gotto A. M. JR. and Jackson R. L. (1975) J. Biol. Chem. 7, 2725–2738/, while the other two were identical to the major alternatives known for immunoglobulin light and heavy chains. The light chain corresponds to a typical k chain and the heavy chain, as judged from coincidences with reports of heavy chain structures show maximal fits with several g, m or a chains, and could well be a typical g chain. Although the native of the immunoglobulin chains should not be considered final from a sequence analysis in mixture. The results, nevertheless clearly identify SPAP as composed of three types of protein chain, apolipoprotein Al, and immunoglobulin heavy and light chains without obvious signs of multiplicity. Stoichiometries are difficult to judge since initial yields in the degradation may be slightly different for the chains but a complex between the immunoglobulin and the apolipoprotein molecules yielding equimolar amounts of the chains appears possible.

Figure 1A:
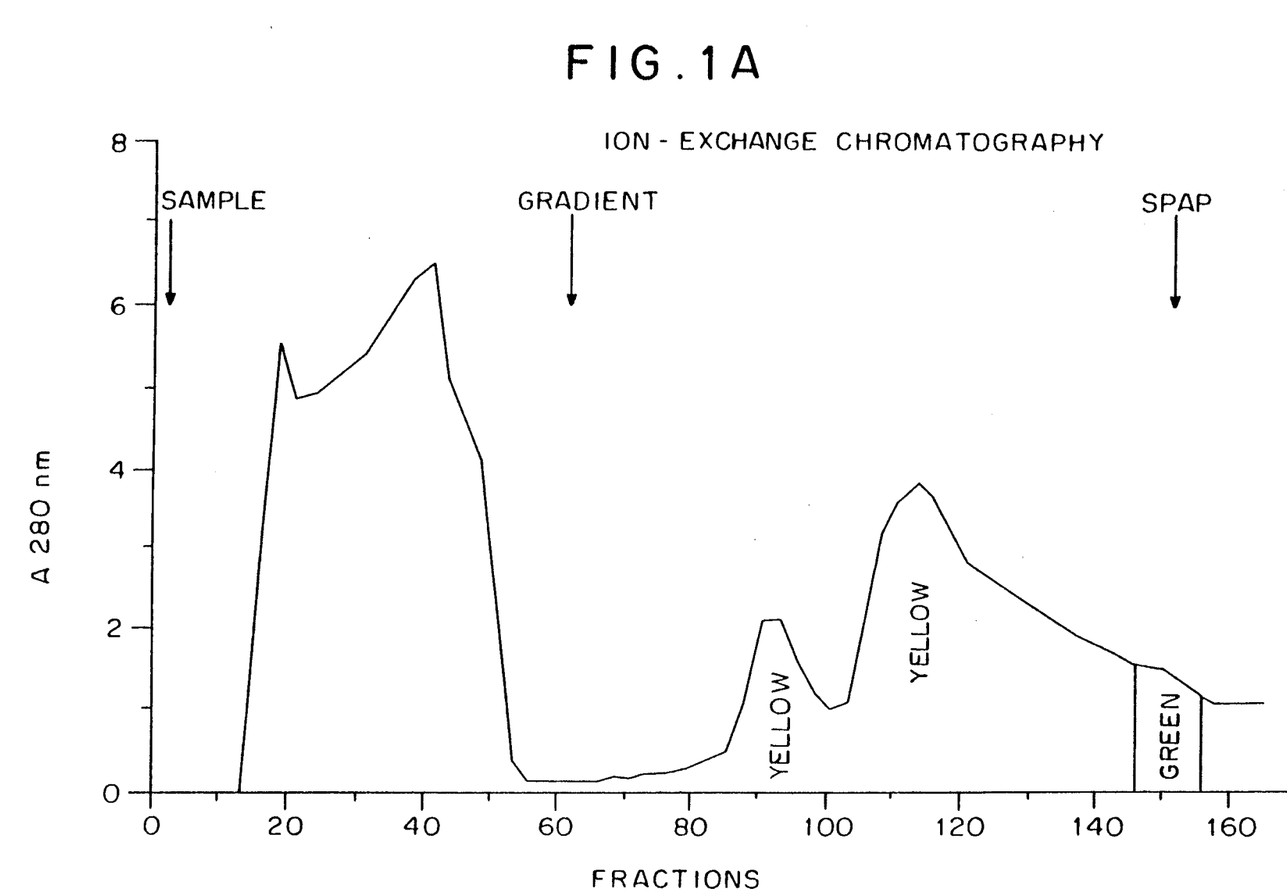
Figure 1B:
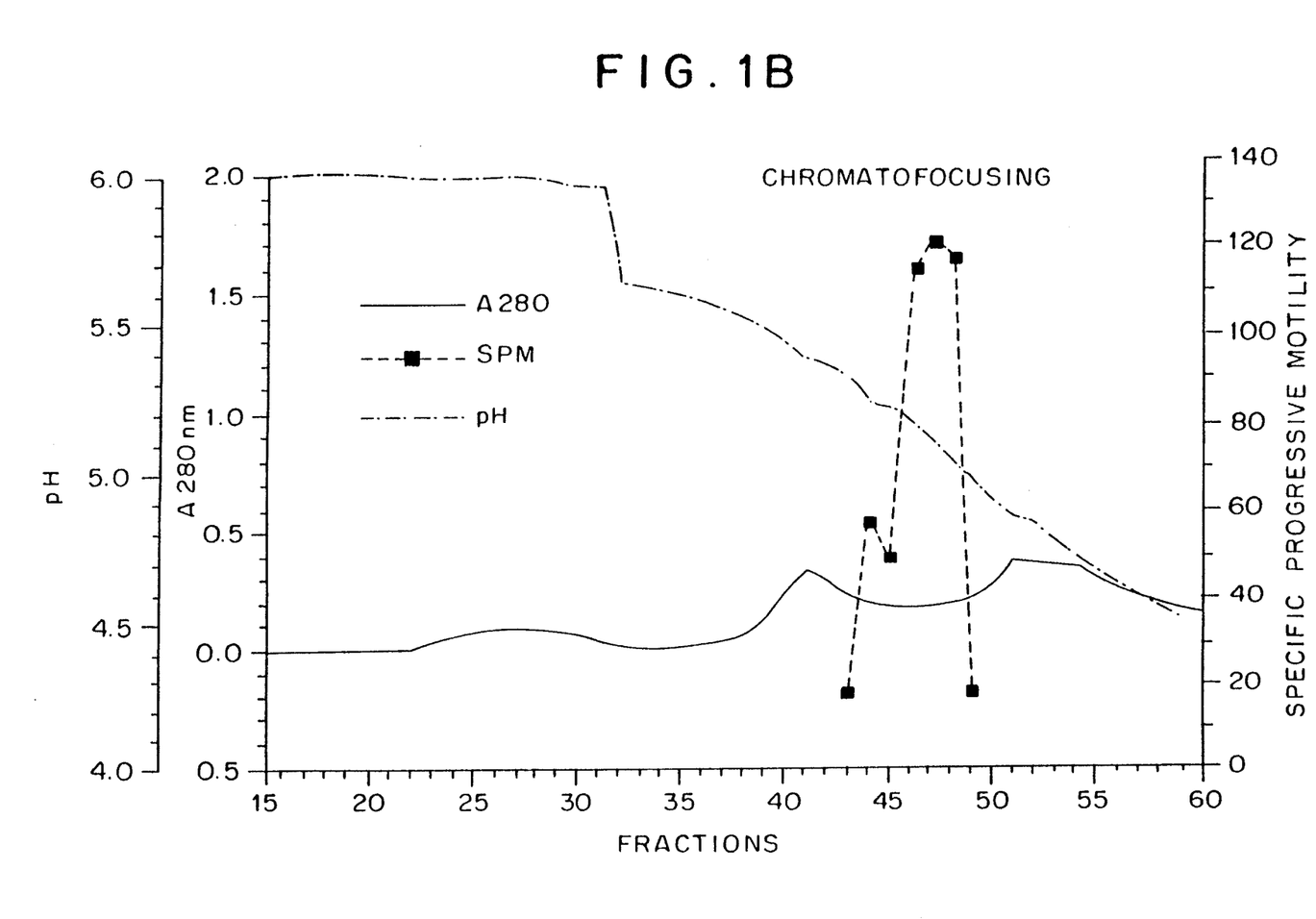
Figure 1C:
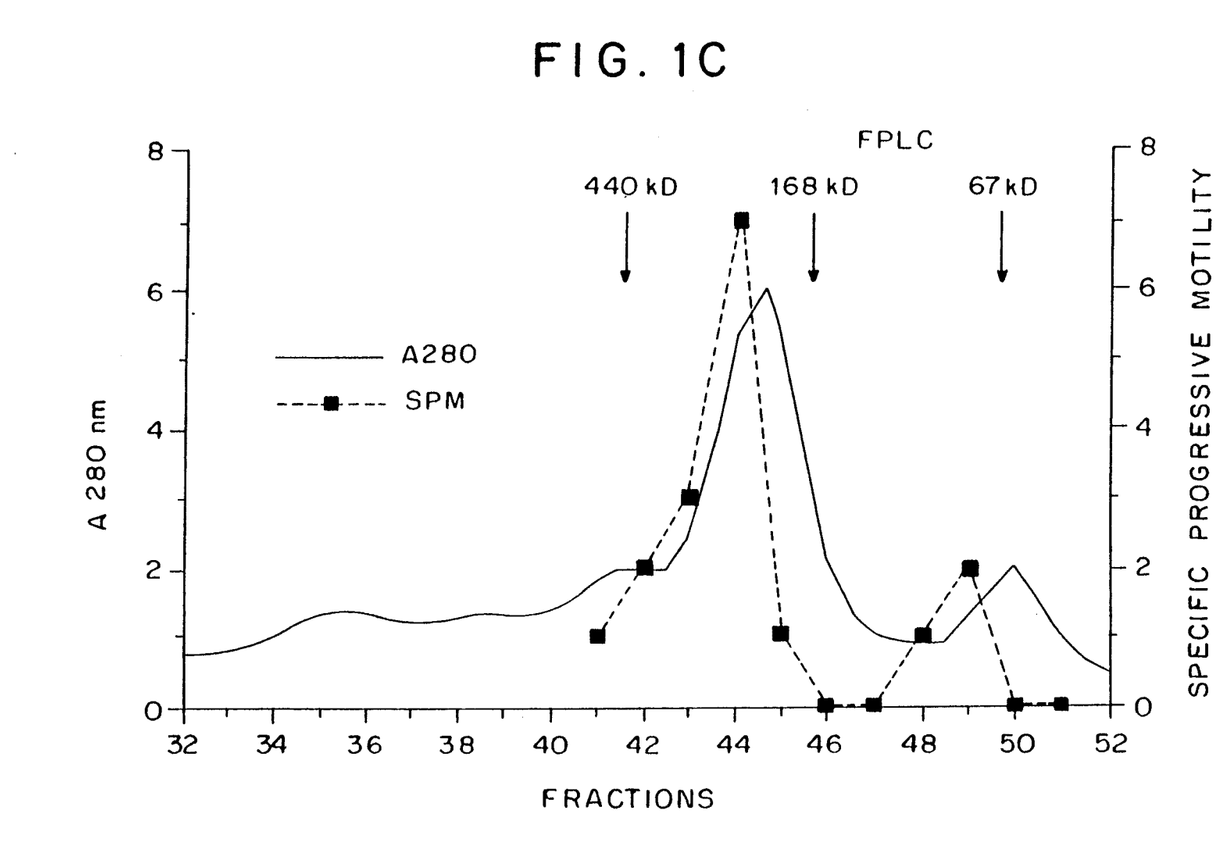
Figure 2:
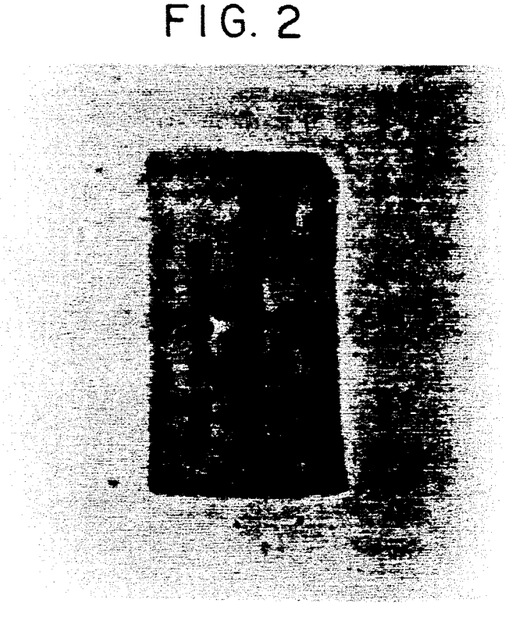
FIG. 2 illustrates sodium dodecyl sulphate (SDS) polyacrylamide gel electrophoresis in the presence of and in the absence of 2-mercaptoethanol and was performed using ready made gels and calibration standards.
Figure 3:
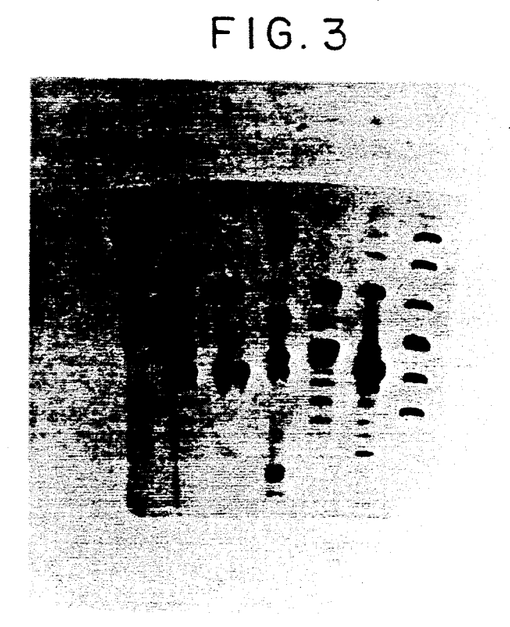
FIG. 3 is illustrating SDS polyacrylamide gel electrophoresis in the presence of 2-mercaptoethanol.
Figure 4A:
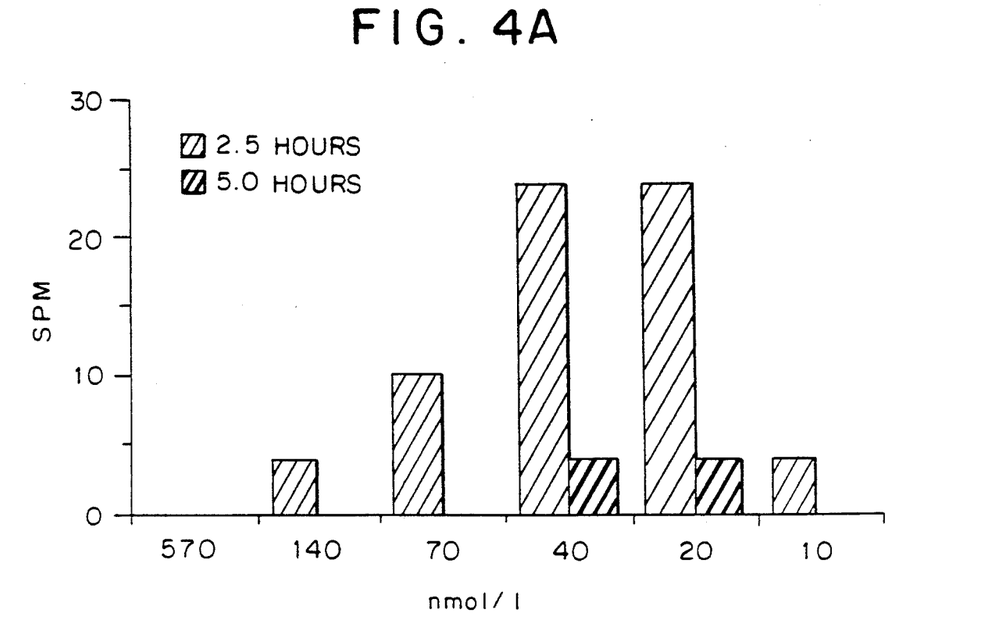
Figure 4B:
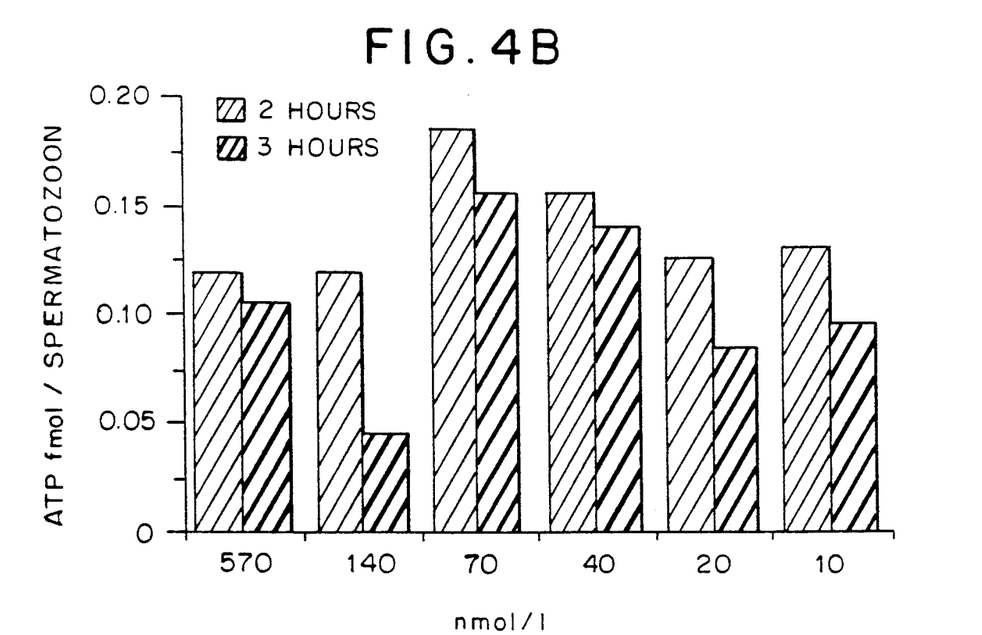

The sperm activating capacity of SPAP is demonstrated as follows:

The eluates from the different purification steps activate spermatozoa to the same extent as 16.7% (v/v) serum. The sperm activating capacity of purified SPAP was found to be dependent on the SPAP concentration. The activation could be detected using SPM as well as ATP (FIGS. 4A–4B). In the "standardized model system" with 2.5 million spermatozoa/ml the maximum effect was obtained at a concentration of 20–70 nmol/l. Purified SPAP heated to 100° C. for 5 minutes did not activate sperm motility. Purified albumin, apolipoprotein Al and immunoglobulins had only minor and short termed (a couple of hours) effects on sperm motility.

The immunization and characterization of anti-SPAP serum was performed by immunizing rabbits with purified SPAP in Freund's complete adjuvant. Ten weeks after immunization antiserum of sufficient titer was detected in one rabbit. When this antiserum was incubated with normal male sera in proportions of about 9:1 (v/v) a precipitate was formed. Analyzes of the supernatant for apolipoprotein Al showed a low apolipoprotein Al content compared with that of untreated sera, suggesting that most of the apolipoprotein Al had been precipitated by the rabbit serum. Compared with untreated human serum, the precipitated human serum showed less capacity (about 25%) to support sperm motility. When rabbit anti-SPAP serum was added directly to spermatozoa in the "standardized model system " the motility was reduced as compared to that seen with the addition of pre-immunized serum.

SPAP antiserum added to spermatozoa was found to inhibit sperm motility. The most likely explanation for this is that SPAP is earlier bound to the spermatozoa and then recognized by the antibodies.

After gel filtration by FPLC® chromatography the molecular weight of the fraction was calculated to be about 250 kD and after Blue Sepharose® the major band observed on SDS polyacrylamide gels, in the absence of 2-mercaptoethanol, corresponded to about 180 kD. The difference is about 70 kD i.e. corresponds to the molecular weight of albumin. SDS polyacrylamide gel electrophoresis, in the presence of 2-mercaptoethanol, revealed the components (50 kD and 25 kD). Stoichiometries of the sperm activating protein are difficult to judge, but a complex between the immunoglobulin and the apolipoprotein molecules yielding equimolar amounts of the chains appear possible. Apolipoprotein Al, immunoglobulins and albumin separately had a minor effect on sperm motility. It appears likely that an apolipoprotein Al-immunoglobulin complex mediates activation of spermatozoa.

The above results show that the major sperm activating capacity in serum is mediated by a fraction with a molecular weight of around 250 kD. This fraction is now shown to be composed of a complex containing albumin, apolipoprotein Al, and immunoglobulin heavy and light chains. As boiling destroyes the activating capacity, it is likely that the effect is mediated by the macromolecule itself rather by a small ligand. As SDS polyacrylamide gel electrophoresis in the absence of 2-mercaptoethanol showed no bands below 150 kD, but components observed in the presence of 2-mercaptoethanol it appears likely that the complex is dependent on intact protein disulphide bridges. The molecular weight of the complex on the FPLC® chromatography was calculated to be about 250 kD. After chromatography on Blue Sepharose®, the band on the SDS polyacrylamide gel corresponded to about 180 kD. The difference is about 70 kD, i.e. could correspond to the molecular weight of albumin. Stoichiometries are difficult to judge but a complex between equimolar amounts of the immunoglobulin and the apolipoprotein appears possible. The molecular weight of this complex should be about 180 kD which is similar to what was found on the gel electrophoresis. Even if the macromolecule without albumin could activate spermatozoa it is believed that the biologically active form thereof contains one molecule of albumin and has a molecular weight of about 250 kD, in agreement with the results of the FPLC®.

Our studies show that the antiserum raised interacts with the macromolecule and with immunoglobulins.

The mechanism by which the macromolecule induces the sperm activation is unknown. Judging from the small amounts required for activation, a receptor-mediated or enzyme-linked mechanism appears likely. In this context, it may be noted that apolipoprotein Al activates lecithin:cholesterol acyltransferase (LCAT), but we have no evidence that this or any other enzyme is involved in sperm activation.

The novel macromolecular complex is probably present also in other extracellular fluids. Thus, it is known that motility is the single most important variable for judging sperm fertilization ability and that different sera and follicular fluids activate sperm non-identically, the macromolecule may be useful both for diagnostic and therapeutic use.

We claim:

1. A protein macromolecule comprising, an essentially pure protein complex of apolipoprotein and immunoglobulin having a molecular weight of about 180,000 to 250,000 Daltons and which is capable of activating sperm motility.

2. The protein macromolecule according to claim 1 further comprising albumin.

3. The protein macromolecule according to claim 2 wherein a ratio of said apolipoprotein, said immunoglobulin and said albumin are in about equimolar amounts.

4. The protein macromolecule according to claim 1 wherein said essentially pure protein complex has an isoelectric point of about 5.1.

5. A pharmaceutical composition comprising an effective amount of an essentially pure protein complex of apolipoprotein and immunoglobulin having a molecular weight of about 180,000 to 250,000 Daltons and which is capable of activating sperm motility, and a pharmaceutically acceptable excipient.

* * * * *